United States Patent [19]

Wilkinson

[11] 4,346,083

[45] Aug. 24, 1982

[54] BIOLOGICALLY ACTIVE AMIDES

[75] Inventor: Samuel Wilkinson, Beckenham, England

[73] Assignee: Burroughs Wellcome Co., Research Triangle Park, N.C.

[21] Appl. No.: 191,150

[22] Filed: Sep. 25, 1980

Related U.S. Application Data

[62] Division of Ser. No. 927,271, Jul. 24, 1978, Pat. No. 4,244,944.

[30] Foreign Application Priority Data

Nov. 24, 1977 [GB] United Kingdom ............... 48980/77

[51] Int. Cl.$^3$ ..................... A61K 37/00; C07C 103/52
[52] U.S. Cl. ............................. 424/177; 260/112.5 R
[58] Field of Search .................. 424/177; 260/112.5 R

[56] References Cited

PUBLICATIONS

S. Bajusz, et al., Acta Biochim et Biophys. Acad. Sci. Hung., vol. 11 (1) 305-309 (1976).
S. Bajusz, et al., Febs Letters, 76(1) 1977, 91-92.

Primary Examiner—Delbert R. Phillips
Attorney, Agent, or Firm—Donald Brown

[57] ABSTRACT

Peptides, acid addition salts, salts, and pharmaceutical compositions thereof, and their use as morphine agonists, and especially Tyr.D.Met.Gly.Phe(4NO$_2$).-ProNH$_2$ and Tyr.D-Met(O).Gly.Phe(4NO$_2$).ProNH$_2$ as anti-diarrhoeals and anti-tussives.

7 Claims, No Drawings

BIOLOGICALLY ACTIVE AMIDES

This is a division of application Ser. No. 927,271, filed July 24, 1978, now U.S. Pat. No. 4,244,944.

This invention relates to peptides and derivatives thereof; to the preparation of such compounds; to formulations containing such compounds and the preparation of such formulations; and to the use of the compounds in human and veterinary medicine.

More particularly the present invention relates to peptides and derivatives thereof which exhibit morphine agonist activity. As generally accepted and as the term is used herein, a morphine agonist is a compound the biological activity of which mimics that of the natural alkaloid.

The pharmacological properties and therapeutic uses of morphine are well documented in the literature, see for example "The Pharmacological Basis of Therapeutics", Goodman, L. S. and Gilman, A. eds., published by The MacMillan Company, New York, third edition (1965) especially at Chapter 15, pages 247 to 266, and "Martindale: The Extra Pharmacopoeia", Blacow, N. W. ed., published by The Pharmaceutical Press, London, twenty-sixth edition (1972) especially at pages 1100 to 1106, all of which is incorporated herein by reference hereto. As is well known however (Goodman, L. S. et al., loc. cit, Chapter 16) repeated administration of morphine can lead to the recipient developing an addiction to the drug and tolerance to its effects and to his manifesting withdrawal symptoms when administration is discontinued. For many years therefore research has been conducted with the aim of obtaining a compound having the activity spectrum of morphine while lacking its disadvantages.

The present invention provides the novel peptides of formula (I):

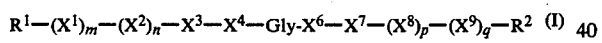

together with their salts and acid addition salts, which compounds exhibit morphine agonist activity in both in vitro and in vivo tests.

In formula (I):

$R^1$ is hydrogen or alkyl;

$X^1$ and $X^2$ are the same or different and each is the radical of a basic amino acid (D or L);

$X^3$ is an L-radical of formula

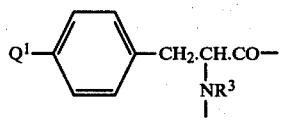

where $Q^1$ is selected from hydroxy, alkoxy, alkanoyloxy, alkyl, nitro, trifluoromethyl, amino, N-alkylamino, N,N-dialkylamino, halogen and benzyloxy and $R^3$ is hydrogen or alkyl;

$X^4$ is a D-radical of formula

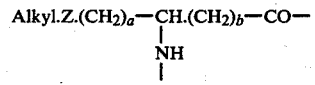

where the Alkyl has 1 to 3 carbon atoms, Z is selected from —O—, —S—, —SO— and —$SO_2$—, a is 1, 2 or 3 and b is 0 or 1;

$X^6$ is an L-radical of formula

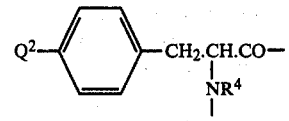

where $Q^2$ is selected from hydroxy, alkoxy, alkanoyloxy, alkyl, nitro, trifluoromethyl, amino, N-alkylamino, N,N-dialkylamino, halogen, benzyloxy, methyl sulphide, methyl sulphoxide, methylsulphone and hydrogen and $R^4$ is hydrogen or alkyl;

$X^7$ is selected from L-prolyl, L-hydroxyprolyl, L-homoprolyl, L-pipecolinyl, L-threonyl, L-seryl, cycloleucyl, D-prolyl, D-hydroxyprolyl, D-methionyl, D-methionyl sulphoxide, D-methionyl sulphone, D-isoleucyl, D-norleucyl, D-valyl, D-norvalyl, D-seryl, D-threonyl, D-homoprolyl, D-pipecolinyl and D-alanyl;

$X^8$ and $X^9$ are the same or different and each is selected from seryl (D or L) and threonyl (D or L);

$R^2$ is selected from a group —$OR^5$, where $R^5$ is hydrogen or alkyl, and a group —$NR^6R^7$ where $R^6$ and $R^7$ are the same or different and each is selected from hydrogen, alkyl and benzyl or $R^6$, $R^7$ and the nitrogen atom to which they are attached together comprise a group selected from pyrrolidino, piperidino and morpholino; or $R^2$ represents a group, replacing the 1-carboxyl group of the C-terminal amino acid residue, of formula —$CH_2OR^8$ where $R^8$ is hydrogen or alkanoyl; and m, n, p and q are each selected from 0 and 1; provided that when m, n, p and q are each 0;

$R^1$ is hydrogen;

$X^3$ is L-tyrosyl;

$X^4$ is D-methionyl, D-methionyl sulphoxide or D-methionyl sulphone;

$X^6$ is L-phenylalanyl, -4-nitrophenylalanyl, L-4-chlorophenylalanyl or L-4-methylphenylalanyl;

$X^7$ is L-prolyl, D-prolyl, D-methionyl, D-methionyl sulphoxide, D-methionyl sulphone, D-leucyl or cycloleucyl;

then $R^2$ is other than a group —$NR^6R^7$ wherein one of $R^6$ and $R^7$ is hydrogen and the other is alkyl or benzyl or wherein $R^6$, $R^7$ and the nitrogen atom to which they are attached together comprise a morpholino, piperidino or pyrrolo radical group;

furthermore that when $X^6$ is L-phenylalanyl and $X^7$ is L-prolyl then $R^3$ is a group -$CH_2OR^8$ as above defined.

The abbreviations used herein for amino acids and their radicals are those conventional in the art and may be found in, for example, *Biochemistry*, 11, 1726 (1972). In the above and throughout the following all references are to the L-amino acids and their radicals except in the case of glycine and unless otherwise stated.

By the term "basic amino acid" is herein meant an amino acid having two basic functions and one carboxyl group, and as examples of the radicals $X^1$ and $X^2$ may be mentioned lysyl (D and L), homoarginyl (D and L), ornithyl (D and L), histidyl (D and L), α,γ-diaminobutyryl (D and L) and arginyl (D and L).

In formula (I) the alkyl identities for $Q^1$, $Q^2$, $R^1$, $R^3$, $R^4$, $R^5$, $R^6$ and $R^7$, the alkyl moiety or moieties of the alkoxy, alkanoyloxy, N-alkylamino and N,N-dialkylamino identities for $Q^1$ and $Q^2$ and the alkyl moiety of the alkanoyl identity for $R^8$ desirably each have 1 to 4 carbon atoms and preferably 1 or 2 carbon atoms, i.e. methyl or ethyl. In the N,N-dialkylamino identities for $Q^1$ and $Q^2$ the alkyl moieties may be the same or different. The halogen identities for $Q^1$ and $Q^2$ may each be selected from fluorine, chlorine, bromine and iodine.

Amongst the identities for $X^4$ may particularly be mentioned the following radicals:

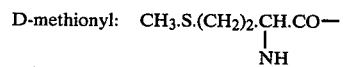
D-methionyl: $CH_3.S.(CH_2)_2.CH.CO-$
NH

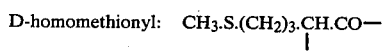
D-homomethionyl: $CH_3.S.(CH_2)_3.CH.CO-$
NH

D-β-homomethionyl: $CH_3.S.(CH_2)_2.CH.CH_2.CO-$
NH

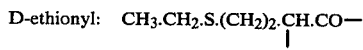
D-ethionyl: $CH_3.CH_2.S.(CH_2)_2.CH.CO-$
NH

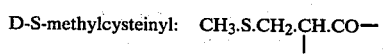
D-S-methylcysteinyl: $CH_3.S.CH_2.CH.CO-$
NH

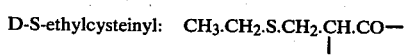
D-S-ethylcysteinyl: $CH_3.CH_2.S.CH_2.CH.CO-$
NH together with the corresponding sulphoxides and sulphones.

In the acid addition salts of the peptides of formula (I) the activity resides in the base and the acid is of less importance although for therapeutic purposes it is preferably pharmacologically and pharmaceutically acceptable to the recipient. Examples of such suitable acids include (a) mineral acids: hydrochloric, hydrobromic, phosphoric, metaphosphoric, nitric and sulphuric acids; (b) organic acids: tartaric, acetic, citric, malic, lactic, fumaric, benzoic, glycollic, gluconic, gulonic, succinic and arylsulphonic, for example p-toluenesulphonic, acids. The pharmaceutically and pharmacologically acceptable acid addition salts together with those salts which are not so acceptable (for example salts of hydrofluoric and perchloric acids) have utility in isolation and purification of the bases, and of course the unacceptable salts are also valuable in the preparation of the acceptable salts by techniques well known in the art. Those peptides containing a plurality of free amino groups may be obtained in the form of mono- or poly-acid addition salts, or as mixed salts of a plurality of acids.

Likewise in the salts of the peptides (comprising the peptide as the carboxylate anion together with a cation) the identity of the cation is of less importance although for therapeutic purposes it is preferably pharmacologically and pharmaceutically acceptable to the recipient. Examples of such suitable cations include sodium and potassium.

The morphine agonist properties of the peptides of formula (I) and their salts and acid addition salts include the following, which are given solely by way of illustration and should be understood to be non-limiting.

(A) In vitro:
(i) Inhibition of neurally evoked contractions of the isolated mouse vas deferens when tested by the method of Hughes et al (Brain Research, 88 (1975) 296) (using pulses at 0.1 Hz), the inhibition being abolished by the known narcotic antagonist naloxone (1-N-allyl-7,8-dihydro-14-hydroxy normorphinone).
(ii) Reduction of electrically-induced contractions of the isolated guinea-pig ileum when prepared for stimulation after the manner of Paton (Brit. J. Pharmacol., 12 (1957) 119–127). (Each intestinal segment was impaled by the anode and suspended with a 2-3 g load. Stimulus parameters: frequency: 0.1 Hz; duration: 0.4 ms; voltage (supramaximal) 30–40 V; the contractions were transduced isotonically).

(B) In vivo:
(i) The compounds exhibit analgesic activity, for example they are effective in mice in the "hot plate" procedure standard in the art when tested by a modification of the method of Eddy, N. B. et al. (J. Pharm. Exp. Therap. 107, 385 (1953)), the compounds being administered by intracerebronventricular injection, and this activity is abolished by naloxone.

As a further example the compounds are effective in reducing acetic acid-induced writhing in mice when tested by a modification of the method of Henderson et. al., J. Pharm. Exp. Therap. 125 (1959), 237; the compounds being administered orally and this reduction in writhing is abolished by naloxone.
(iii) The compounds exhibit antitussive activity, for example when tested in guinea-pigs according to the method of Boura et al. Brit. J. Pharmacol., 39, (1970) 225.
(iv) The compounds exhibit antidiarrhoeal activity, for example they are effective in reducing castor oil-induced diarrhoea in rats.

The peptides of formula (I), their salts and acid addition salts when assessed by a number of standard pharmacological procedures, have also been found both to induce and to maintain anaesthesia in laboratory animals including rats and mice. The compounds are effective in this respect when administered by a variety of routes including parenteral, for example by intravenous or intracerebroventricular injection. Illustrative of the anaesthetic effects of the compounds are the following, which should be understood to be non-limiting.
(i) Abolition of the righting reflex. This is characteristic of recognised anaesthetic agents such as chloral hydrate (2,2,2-trichloro-1,1-ethanediol), urethan (ethyl carbamate) and the barbiturates (derivatives of barbituric acid). An animal lacking this reflex does not roll over or attempt to regain its normal posture when placed on its back.
(ii) Abolition of the pinnal reflex. In this procedure a wire or similar probe is introduced into the ear pinna; in the normal (control) animal there is a resultant reflex twitch or shake of the affected pinna.

(iii) Abolition of the corneal reflex. In this procedure the cornea is lightly touched with a wire or similar; in the normal (control) animal there is a resultant reflex blink of the eyelids. This reflex is of clinical importance in man in that it is one of the last reflexes to be abolished during the induction of general anaesthesia.

Each of the foregoing effects (i), (ii) and (iii) may be reversed by administration of the known narcotic antagonist naloxone (1-N-allyl-7,8-dihydro-14-hydroxynormorphinone). However it has been found that morphine itself does not abolish the righting reflex in laboratory animals such as mice when administered in up to lethal doses.

Thus the ability of the peptides of formula (I) and their salts and acid addition salts both to induce and to maintain anaesthesia is not a morphine-like property.

As subclasses of the peptides of formula (I) and their salts and acid addition salts may be mentioned those compounds wherein:

(i) $R^1$ is hydrogen;
(ii) m and n are both 0;
(iii) $X^3$ is L-tyrosyl;
(iv) $X^4$ is selected from D-methionyl, D-methionyl sulphoxide and D-methionyl sulphone, preferably from D-methionyl and D-methionyl sulphoxide and is desirably D-methionyl sulphoxide;
(v) $X^6$ is selected from L-phenylalanyl and L-4-nitrophenylalanyl and is preferably L-4-nitrophenylalanyl;
(vi) $X^7$ is selected from L-prolyl and D-prolyl and is preferably L-prolyl;
(vii) p and q are both 0; and
(viii) $R^2$ is selected from $-OR^5$ where $R^5$ is preferably hydrogen, $-NHR^7$ where $R^7$ is preferably selected from hydrogen and alkyl and is desirably hydrogen, and $-CH_2OR^8$ where $R^8$ is preferably hydrogen.

As a further subclass may be mentioned those peptides and their salts and acid addition salts of the formula:

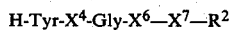

wherein
$X^4$ is selected from D-methionyl, D-methionyl sulphoxide and D-methionyl sulphone;
$X^6$ is selected from L-phenylalanyl, L-4-chlorophenylalanyl and L-4-nitrophenylalanyl;
$X^7$ is selected from D-prolyl, L-prolyl, L-prolinol, D-leucyl, D-methionyl sulphoxide and cycloleucyl; and
$R^2$ is as defined in formula (I).

As a further subclass may be mentioned those peptides and their acid addition salts of formula:

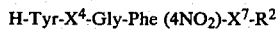

wherein,
$X^4$ is selected from D-methionyl sulphoxide and D-methionyl sulphone;
$X^7$ is selected from L-prolyl, D-prolyl and L-prolinol; and
$R^2$ is selected from amino and monoalkylamino of one to four carbon atoms.

The peptides of formula (I) and their salts and acid addition salts may be prepared by any of the methods known in the art for the preparation of compounds of analogous structure. Thus they may be formed by the sequential coupling of appropriate amino acids using either classical methods of peptide synthesis or solid phase procedures, or by the initial preparation and subsequent coupling of peptide subunits.

Such reactions may be effected by, for example, activating the carboxylic acid group of the ingoing amino acid and protecting the non-reacting amino and carboxylic acid groups. Such techniques are standard in the peptide art. Details of suitable activating and protecting (masking) groups and of suitable reaction conditions (both for the coupling reactions and for the removal of protecting groups) giving the minimum of racemisation may be found in the following literature, all of which is incorporated herein by reference hereto, which is given purely by way of exemplification and which is intended to be neither exhaustive nor limiting.

(a) Published United Kingdom patent specifications Nos. 1 042 487; 1 048 086; and 1 281 383.
(b) Schröder and Lüebke, "The Peptides" (Academic Press) (1965).
(c) Bellean and Malek, *J. Am. Chem. Soc.*, 90, 165 (1968).
(d) Tilak, *Tetrahedron Letters*, 849 (1970).
(e) Beyerman, *Helv. Chim. Acta.*, 56, 1729 (1973).
(f) Stewart and Young, "Solid Phase Peptide Synthesis" (W. H. Freeman and Co.) (1969).

Depending upon the reaction conditions the peptides of formula (I) are obtained in the form of the free base or as an acid addition salt or salt thereof. The acid addition salts may be converted into the free bases or salts of other acids, and the bases may be converted into acid addition salts thereof, by techniques well known in the art. Likewise the peptides may be converted to salts thereof, and the salts converted to the peptides or to other salts, by well established techniques.

The peptides of formula (I) and their salts and acid addition salts may thus be prepared by condensing a reagent (II)

wherein $Y^1$ is selected from the radical $(X^1)_m$ as defined in formula (I) and a partial radical sequence having the radical $(X^1)_m$ at its N-terminal end and from thereon corresponding to formula (I), with a reagent (III)

wherein $Y^2$ corresponds to the balance of the above defined product, the reagents (II) and (III) being optionally protected and/or activated where and as appropriate; followed if necessary and as appropriate by one or both of the steps of deprotection of the product and conversion of the product into the base or a salt or an acid addition salt thereof.

It will be appreciated by those skilled in the peptide art that the arginyl (D or L) and homoarginyl (Har) (D or L) radicals may not only be incorporated into the peptide chain in the fashion described above but may also be formed in situ in the assembled chain, or in a subunit thereof, by guanidation of an ornithyl (D or L) or lysyl (D or L) radical respectively, using a reagent such as 1-guanyl-3,5-dimethylpyrazole.

It will also be appreciated that other in situ conversions of the peptides of formula (I) are possible. Thus the peptides wherein $R^2$ is a group $-NR^6R^7$ may be prepared by for example reaction of a peptide alkyl ester (wherein $R^2$ is $-OR^5$ where $R^5$ is alkyl) such as the methyl ester with ammonia, a heterocyclic base or a mono- or diamine, as appropriate. The peptide esters may be prepared from the peptide acids ($R^2$ is $-OR^5$ where $R^5$ is hydrogen) by standard esterification procedures and the esters may be converted to the peptide acids by saponification. A hydroxy group $Q^1$ or $Q^2$ in respectively the radical $X^3$ or $X^6$ may be converted to an alkoxy or benzyloxy group by the use of the appropriate diazoalkane, for example diazomethane to provide a methoxy group. Benzyloxy and alkanoyloxy identities for $Q^1$ and $Q^2$ may be converted to hydroxy groups by hydrogenolysis in methanol using 10% palladium on charcoal catalyst and by alkaline hydrolysis respectively, and a hydroxy group may be converted to an alkanoyloxy group by standard alkanoylation procedures. All these are conventional techniques in the peptide art and reference may be made to the literature referred to hereinabove for details of reaction conditions and of appropriate protection/deprotection procedures.

Because of their morphine agonist activity already alluded to the peptides of formula (I) together with their pharmacologically and pharmaceutically acceptable salts and acid addition salts may be used in the treatment of mammals in the fields of both human and veterinary medicine in any condition where an agent with a morphine-like effect is indicated. Specific utilities that may be mentioned, by way of example, include the following:

(1) The relief of pain (analgesia), for example pain arising from spasm of smooth muscle as in renal or biliary colic, pain due to terminal illness such as cancer, pain in the post-operative period, and obstetrical pain.
(2) Sedation, for example in pre-anaesthetic medication; tranquillization; the induction of sleep, especially where sleeplessness is due to pain or cough; and the relief of anxiety in general.
(3) The suppression of cough.
(4) The relief of dyspnoea, for example that of acute left ventricular failure or pulmonary oedema.
(5) The induction of constipation, for example after ilcostomy or colostomy, and the treatment of diarrhoea and dysentery.
(6) The induction of euphoria and the treatment of depression, for example when allied to the relief of pain in terminal illness such as cancer.

The peptides of formula (I) and their pharmacologically and pharmaceutically acceptable salts and acid addition salts may also be used in the fields of both human and veterinary medicine for the induction and/or maintenance of anaesthesia in a mammal.

A peptide or a salt thereof may be administered either alone as the sole anaesthetic agent or in combination with one or more other substances which may complement and/or supplement its activity. Such additional substances may be administered before, simultaneously with or after administration of the peptide or salt thereof and in the case of simultaneous administration the various agents may be administered either as separate doses or as a combination formulation.

As one possibility the peptide or salt thereof may be administered subsequent to administration of a benzodiazepine tranquillizer such as chlordiazepoxide (7-chloro-2-methylamino-5-phenyl-3H-1,4-benzodiazepine 4-oxide), diazepam(7-chloro-1,3-dihydro-1-methyl-5-phenyl-2H-1,4-benzodiazepin-2-one) and oxazepam(7-chloro-1,3-dihydro-3-hydroxy-5-phenyl-2H-1,4-benzodiazepin-2-one).

As another possibility the peptide or salt thereof may be administered for the maintenance of anaesthesia after this has been initially induced by the previous administration of another anaesthetic agent, for example a barbiturate such as thiopental sodium (sodium 5-ethyl-5-(1-methylbutyl)-2-thiobarbiturate).

A particular utility for the peptides of formula (I) and their pharmacologically and pharmaceutically acceptable salts and acid addition salts, within the field of anaesthesia, is the induction and/or maintenance of the state referred to as "neuroleptanalgesia", a condition characterised by quiescence, psychic indifference to environmental stimuli, and analgesia (see, for example, Dorland's Illustrated Medical Dictionary, twenty-fifth edition, published by W. B. Saunders, 1974, at page 1041, and *The Pharmacological Basis of Therapeutics*, Goodman, L.S. and Gilman, A. eds., fifth edition, published by Macmillan Publishing Co. Inc., 1975, especially at Chapter 8, pages 97 to 101, all of which is incorporated herein by reference hereto). This condition is recognised by clinicians as desirable for enabling the performance of procedures such as bronchoscopy, X-ray studies, burn dressings and cystoscopy wherein a degree of patient cooperation is of value, and a fixed-dose combination comprising the narcotic analgesic phentanyl citrate (N-(1-phenethyl-4-piperidyl) propionanilide citrate) and the neuroleptic agent droperidol (1-{1-[3-(p-fluorobenzoyl)propyl]-1,2,3,6-tetrahydro-4-pyridyl}-2-benzimidazolinone) has found acceptance for use in such circumstances.

In veterinary medicine two fixed-dose combinations comprising the narcotic analgesic etorphine hydrochloride (4,5α-epoxy-3-hydroxy-6-methoxy-α,17-dimethyl-α-propyl-6,14-ethenomorphinan-7α(R)-methanol hydrochloride) together with either acepromazine (1-[10-[3-(dimethylamino)propyl]-10H-phenothiazin-2-yl]ethanone) or methotrimeprazine (2-methoxy-N,N,β-trimethyl-10H-phenothiazine-10-propanamine) have found acceptance for use in circumstances wherein a neuroleptanalgesic effect is required, for example in fracture reduction, wound stitching and castration.

Heretofore neuroleptanalgesia has been achievable only upon administration of such a drug combination as above mentioned. The peptides of formula (I) and their acceptable salts and acid addition salts are thus an important clinical advance and valuable addition to the armamentarium of the medical and veterinary professions in alone enabling this result, without any additional medication being required.

For each of the utilities recited hereinbefore for the peptides of formula (I) and their salts and acid addition salts, that is to say, whether for use for the induction and/or maintenance of anaesthesia (for example the induction and/or maintenance of neuroleptanalgesia) or for use in a condition where an agent with a morphine-like effect is indicated (for example the utilities specifically identified hereinbefore under (1), (2), (3), (4), (5) or (6)) the amount required of the peptide or salt or acid addition salt thereof (hereafter referred to as the active ingredient) will vary with the route of administration and with the nature and required extent of the desired effect, and will ultimately be at the discretion of the physician or veterinarian. In general however for each of these utilities the dosage will be in the range 0.0025 μg to 40 mg per kilogram bodyweight of mammal, preferably 0.025 μg to 10.0 mg/kg, more preferably 0.01 μg of 4.0 mg/kg and optimally 0.25 to 400 μg/kg (all dosages calculated with reference to the peptide base). For use as an anti-diarrhoeal, an effective oral dose for humans is a 3 mg. single dose given two or three times daily; for anti-tussive use an effective oral dose is 30 mg. single dose given two or three times daily.

The active ingredients may be administered by any route appropriate to the effect to be achieved, suitable routes including oral, rectal, nasal, topical (buccal), vaginal and parenteral (including subcutaneous, intramuscular and intravenous). It will be appreciated that the preferred route will vary with the effect to be achieved and thus for example in the relief of obstetrical pain administration directly into the spinal cord may be advantageous.

While it is possible for the active ingredients to be administered as the raw chemical it is preferable to present them as a pharmaceutical formulation preparation.

The formulations, both veterinary and for human use, of the present invention comprise an active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof. Desirably the formulations should not include oxidising agents and other substances with which peptides are known to be incompatible.

The formulations include those suitable for oral, rectal, nasal, topical (buccal), vaginal or parenteral (including subcutaneous, intramuscular and intravenous) administration, although the most suitable route in any given case will depend upon for example the active ingredient and the condition to be treated. The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; or as a solution or a suspension in an aqueous liquid or a nonaqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

Formulations for rectal administration may be presented as a suppository with the usual carriers such as cocoa butter, while a suitable formulation for nasal administration is nasal drops comprising the active ingredient in aqueous or oily solution.

Formulations suitable for topical administration in the mouth include lozenges comprising the active ingredient in a flavoured basis, usually sucrose and acacia or tragacanth; and pastilles comprising the active ingredient in an inert basis such as gelatin and glycerin, or sucrose and acacia.

Formulations suitable for vaginal administration may be presented as pessaries, creams, pastes or spray formulations containing in addition to the active ingredient such carriers as are known in the art to be appropriate.

Formulations suitable for parenteral administration conveniently comprise sterile aqueous solutions of the active ingredient, which solutions are preferably isotonic with the blood of the recipient. Such formulations may be conveniently prepared by dissolving solid active ingredient in water to produce an aqueous solution, and rendering said solution sterile and isotonic with the blood of the recipient. The formulations may be presented in unit-or in multi dose containers, for example scaled ampoules or vials.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose.

It should be understood that in addition to the aforementioned ingredients the formulations of this invention may include one or more additional ingredients such as diluents, buffers, flavouring agents, binders, surface active agents, thickeners, lubricants, preservatives (including anti-oxidants) and the like.

Where the formulation, for human or for veterinary use, is presented in unit dosage form, for example those unit dosage forms specifically mentioned above, each unit thereof conveniently contains the active ingredient (as above defined) in an amount in the range 0.125 μg. to 2 g., preferably 1.25 μg. to 200 mg. and optionally 12.5 μg. to 20 mg. (all weights calculated with reference to the peptide base).

It will be appreciated from the foregoing that what we will claim may comprise any novel feature described herein, principally and not exclusively, for example:
 (a) The peptides of formula (I) as hereinabove defined together with their salts and acid addition salts.
 (b) Methods as described hereinabove for the preparation of the peptides of formula (I) and their salts and acid addition salts.
 (c) Pharmaceutical formulations comprising a peptide of formula (I), a pharmacologically and pharmaceutically acceptable salt thereof or a pharmacologically and pharmaceutically acceptable acid addition salt thereof together with an acceptable carrier therefor.
 (d) Methods for the preparation of the pharmaceutical formulations defined in (c) above.
 (e) A method for the treatment of a mammal for a condition wherein an agent with a morphine-like effect is indicated, comprising the administration to the mammal of a treatment effective non-toxic amount of a peptide of formula (I), a pharmacologically and pharmaceutically acceptable salt thereof or a pharmacologically and pharmaceutically acceptable acid addition salt thereof.

(f) A method according to (e) above for the treatment of a condition selected from those specifically identified hereinabove under (1), (2), (3), (4), (5) or (6).

(g) A method for the induction and/or maintenance of anaesthesia in a mammal, comprising the administration to the mammal of an anaesthetic-effective, non-toxic amount of a peptide of formula (I) or a pharmacologically and pharmaceutically acceptable salt or acid addition salt thereof.

(h) A method for the induction and/or maintenance of neuroleptanalgesia in a mammal, comprising the administration to the mammal of a neuroleptanalgesic-effective, non-toxic amount of a peptide of formula (I) or a pharmacologically and pharmaceutically acceptable salt or acid addition salt thereof.

The following Examples serve to illustrate the present invention but should not be construed as in any way providing a limitation thereof. All temperatures are in degrees Celsius.

Experimental Section

The following abbreviations are used throughout
HOBT—1-hydroxybenzotriazole
DCCI—dicyclohexylcarbodiimide
DCU—dicyclohexylurea
NMM—N-methylmorpholine
DMF—dimethylformamide Pr—isopropanol
Pr$_2$O—diisopropyl ether
pe—petroleum ether
EtOAc—ethyl acetate Z—benzyloxycarbonyl
Bu—tertiary butyl
BOC—tertiary butyloxycarbonyl
Bzl—benzyl Peptides were examined by tlc on Merck silica gel plates with the following solvent systems:
1—Methylethylketone
2—n.Butanol:acetic acid:water (3:1:1)
3—Chloroform:methanol:32% acetic acid (120:90:40)
4—Chloroform:methanol:32% ammonia (120:90:40)
5—n.Butanol:acetic acid:ethylacetate:water (1:1:1:1)
6—Chloroform:methanol (8:1)
7—Chloroform:methanol:32% acetic acid (120:90:5)
8—Chloroform:methanol:32% ammonia (120:90:5)

Optical rotations were determined on a Bendix NPL automatic polarimeter. The amino acid compositions of peptide hydrolysates (6 N.HCl at 110° for 24 hours in evacuated sealed tubes) were determined with a Beckman-Spinco Model 120C amino acid analyser or with a Rank Chromostak amino acid analyser.

The following general procedures were used throughout the syntheses of the peptides.

(a) Couplings were carried out in DMF and were mediated by DCCI.

(b) Amino acid ester hydrochlorides were converted to the free esters by addition of a tertiary base, either triethylamine or N-methyl morpholine.

(c) HOBT was added at the coupling stage when segment condensation involved a peptide having an optically active carboxy terminal amino acid.

(d) Couplings were allowed to proceed for 24 hours in the cold room at +4° C.

(e) After coupling, purification was effected by washing with acid and base to remove unchanged reactants.

(f) Alkaline saponifications were carried out in aqueous methanol with an autotitrator at pH 11.5 to 12.0 with N.NaOH.

(g) Benzyloxycarbonyl protecting groups were removed by hydrogenolysis in methanol/acetic acid with 10% palladium on charcoal.

(h) The resulting acetate salts from the above hydrogenolysis were converted to the corresponding hydrochlorides by an addition of methanolic hydrogen chloride.

(i) Benzyl protecting groups were removed by hydrogenolysis in methanol with 10% palladium on charcoal.

(j) Tertiary butyl and tertiary butyloxycarbonyl protecting groups were removed with N-hydrogen chloride in acetic acid, in the presence of anisole to act as a scavenger. Cleavage was allowed to proceed for 60 to 90 minutes.

(k) OBu protecting groups on the alcoholic functions of threonine and serine were removed with trifluoroacetic acid containing 10% water, cleavage being allowed to proceed for 90 minutes.

(l) The final peptides were isolated as their hydrochlorides and were lyophilised from aqueous solution.

EXAMPLE 1

H. Tyr. D-Met. Gly. Phe(4NO$_2$). Pro.NH$_2$

This was prepared according to the Scheme set out in Table 1. The product was first isolated as the hydrochloride addition salt and then purified on carboxymethylcellulose (CMC 52) by gradient elution with ammonium acetate buffers (0.001 M to 0.5 M). After lyophilisation from aqueous solution the acetate addition salt had the following characterising data:
Rf: 0.52$^2$; 0.83$^3$; 0.47$^8$.
$[\alpha]_D^{25}$: +8.1° (C=0.2 in methanol).

EXAMPLE 2

H. Tyr. D-Met(O), Gly. Phe(4NO$_2$). Pro.NH$_2$

This was obtained from the acetate addition salt of Example 1 by oxidation with hydrogen peroxide in glacial acetic acid. The product, as the acetate addition salt, had the following characterising data after lyophilisation from aqueous solution:
Rf: 0.40$^2$; 0.68$^4$.
$[\alpha]_D^{25}$: +6.1° (C=0.12 in methanol).

The following peptides were prepared, with the characterising data respectively shown therefor, according to standard procedures in peptide chemistry analogous to those set out in the foregoing Examples. C-Terminal derivatives are indicated according to convention, that is to say:
—NH$_2$: amide
—NHEt: ethylamide
—OMe: methyl ester In the C-terminal residue (Pro.ol, i.e. prolinol) of the compounds of Examples 7 and 9 the 1-carboxyl group of the conventional prolyl radical is replaced by —CH$_2$OH. In the preparation of these compounds the -Pro.ol group was introduced by reacting the appropriate complementary reagent with H.Pro.ol, prepared by reduction of proline methyl ester (H. Pro. OMe) with sodium borohydride. The final intermediate was in each case the corresponding BOC-tyrosyl pentapeptide which was deprotected by reaction with trifluoroacetic acid in the presence of anisole.

The following procedure illustrates the preparation of analogues of phenylalanine substituted in the para position by the sulphur containing residues CH₃.S—; CH₃.SO— and CH₃.SO₂—.

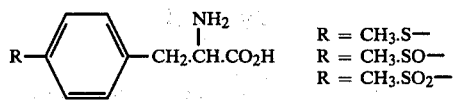

which are present in the peptides of Examples 17, 18 and 19:

The DL amino acids were prepared by the method of Colescott et al. J.A.C.S. 79, 4232 (1957) (copy attached). The routes are outlined below and the number given to each compound corresponds to that used in the above paper.

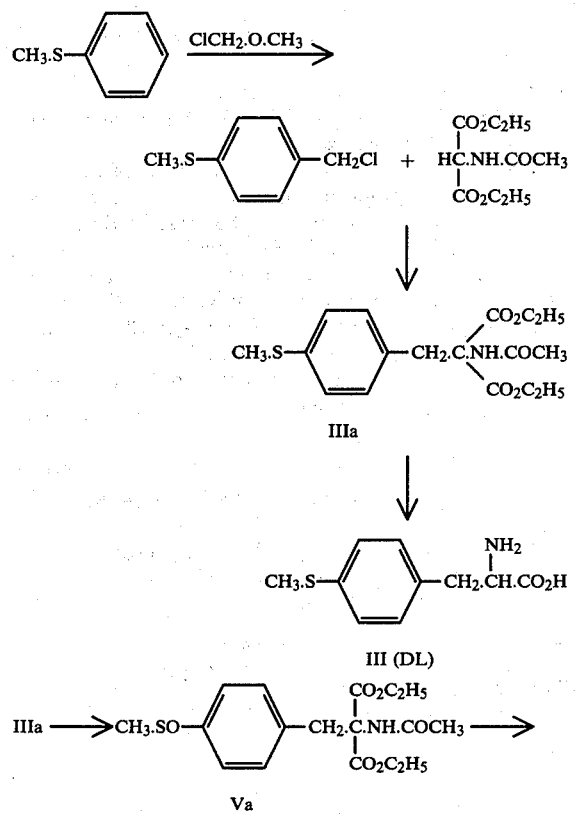

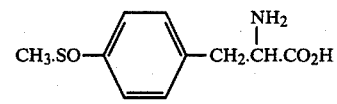

V (DL)

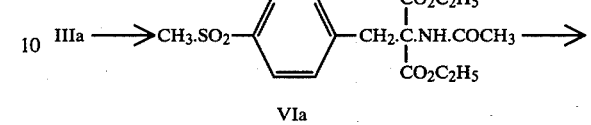

VIa

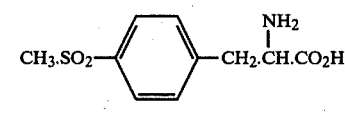

VI (DL)

Each of the DL amino acids was acetylated and resolved by the use of hog renal acylase to give the L-amino acid and the D-acetyl amino acid. [Biochim. Biophys.Acta 148, 414 (1967). Helv.Chim.Acta 59, 2181 (1976).]

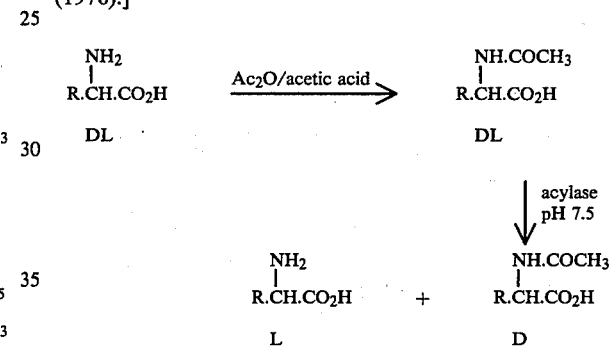

The following illustrates the enzymic resolution of N-acetyl-p-methyl sulphinyl-DL-phenylalanine:

The acetyl-DL-amino acid (6.75 g, 25 millimoles) was dissolved in 150 mls of water and the pH was adjusted to 7.5 by the addition of N ammonium hydroxide solution. Acylase (50 mg) and cobalt acetate (200 mg) were added and the mixture was stirred gently at 38° C. overnight.

The pH was adjusted to 5.5 by the addition of acetic acid and the solution was passed through a 4×30 cm column of Dowex AG 50×2 resin. After the column had been washed with water the L-amino acid was eluted with 0.5 m ammonia.

The L-amino acids were converted to their t-butyloxycarbonyl derivatives and incorporated into the peptide chain by the normal methods of peptide chemistry. The general method is shown in the Scheme below. The various coupling stages may either be mediated by DCCI/HOBT or carried out by the mixed anhydride procedure

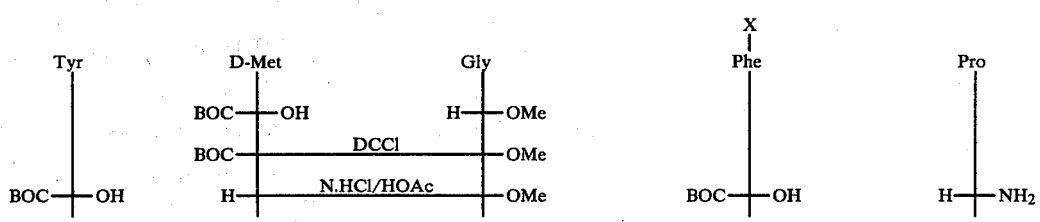

-continued

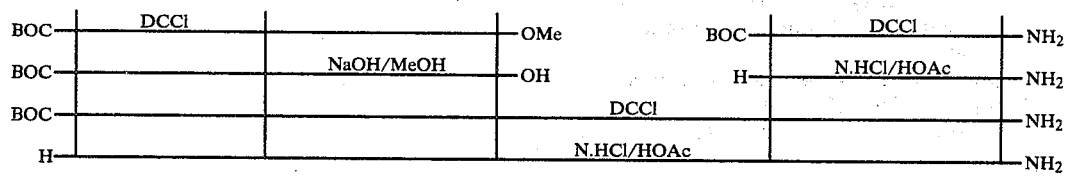

The following illustrates the preparation of analogues containing L-(−)-pipecolinic acid (L-(−)-hexahydropyridine-2-carboxylic acid):

The synthesis of the peptide of Example 12 requires as an intermediate the amide of L-(−)-pipecolinic acid. This was obtained according to the Scheme below:

Picolinic acid (pyridine-2-carboxylic acid)

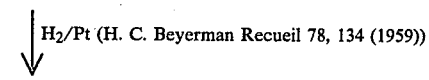

H₂/Pt (H. C. Beyerman Recueil 78, 134 (1959))

Pipecolinic acid

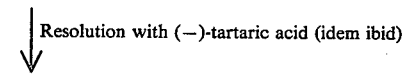

Resolution with (−)-tartaric acid (idem ibid)

L-(−)-pipecolinic acid mp. 268°, [α]$_D^{20}$ = −26.6° (C = 2.85 in H₂O)

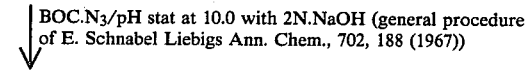

BOC.N₃/pH stat at 10.0 with 2N.NaOH (general procedure of E. Schnabel Liebigs Ann. Chem., 702, 188 (1967))

BOC L-(−)-Pipecolinic acid (m.p. 122°, [α]$_D^{20}$ = 42.0° (C = 1 in MeOH))

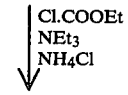

Cl.COOEt
NEt₃
NH₄Cl

BOC.L-(−)-Pec. NH₂ (m.p. 88°, [α]$_D^{20}$ = −34.1° (C = 1.0 in MeOH))

N.HCl/HOAc

-continued

L-(−)-Pec. NH₂.HCl

The synthesis of the peptide of Example 12 then proceeds in similar manner to the Scheme already provided and involves the fragment condensation of:

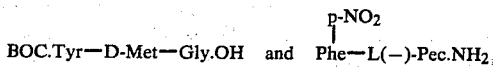

BOC.Tyr—D-Met—Gly.OH and Phe—L-(−)-Pec.NH₂ with p-NO₂ on Phe

The penultimate peptide is therefore;

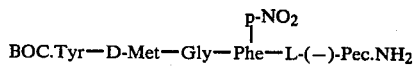

BOC.Tyr—D-Met—Gly—Phe—L-(−)-Pec.NH₂ with p-NO₂ on Phe from which the protecting group is removed by N-hydrogen chloride in glacial acetic acid in the presence of anisole as a scavenger.

The following illustrates the preparation of analogues containing β-homoproline (pyrrolidine-2-acetic acid):

BOC L-proline is homologated as described by M. A. Ondetti and S. L. Engel (J.Med.Chem., 18, 761 (1975)).

BOC.L-homoPro is then converted via the mixed anhydride procedure outlined above to BOC.L-homo-Pro.NH₂ from which L-homoPro.NH₂.HCl is obtained by deprotection with N.HCl/HOAc.

The peptide of Example 21 is prepared in the normal manner from the fragments:

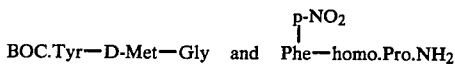

BOC.Tyr—D-Met—Gly and Phe—homo.Pro.NH₂ with p-NO₂ on Phe

The Met residue in position 2 may then be converted to the sulphoxide by treatment with H₂O₂.

H.Tyr————D-Met————Gly————Phe(4NO₂)————Pro.NH₂

BOC.D-Met.OH  H.Gly.OMe

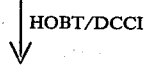

HOBT/DCCI

BOC.D-Met————Gly.OMe

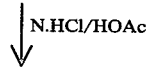

N.HCl/HOAc

BOC.Tyr.OH. H.D-Met————Gly.OMe  BOC.Phe(4NO₂).OH  H.Pro.NH₂

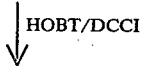

HOBT/DCCI   HOBT/DCCI

BOC.Tyr————D-Met————Gly.OMe  BOC.Phe(4NO₂)————Pro.NH₂

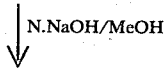

N.NaOH/MeOH   N.HCl/HOAc

-continued

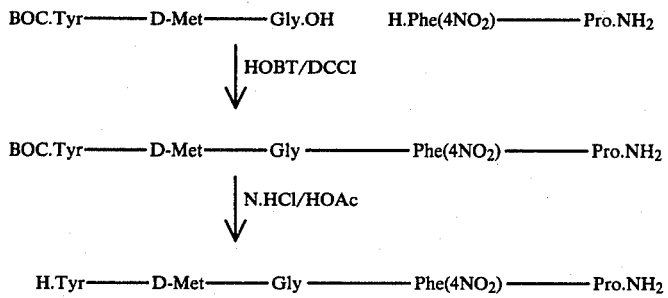

TABLE 1

| Ex. No. | Compound | Rf | $[\alpha]_D^{25}$ (in methanol) |
|---|---|---|---|
| 3. | H.Try.D-Met.Gly.Phe.D-Pro.OH HCl | $0.51^7;0.48^8$ | $+48.3°$ (c = 0.2) |
| 4. | H.Tyr.D-Met.Gly.Phe(4NO$_2$).Pro.OH HCl | $0.44^2;0.46^8$ | $-2.8°$ (c = 0.2) |
| 5. | H.Tyr.D-Met.Gly.Phe(4NO$_2$).Pro.ol trifluoroacetate | $0.56^2;0.75^7;0.71^8$ | $+22.9°$ (c = 0.2) |
| 6. | H.Tyr.D-Met(O).Gly.Phe(4NO$_2$).Pro.ol trifluoroacetate | $0.40^8$ | $+12.9°$ (c = 0.22) |
| 7. | H.Tyr.D-Met(O$_2$).Gly.Phe(4NO$_2$).Pro.NH$_2$ | $0.32^2;0.65^3;0.64^4$ | $+6.3$ (c = 0.2) |
| 8. | H.Tyr.D-Met.Gly.Phe.D-Leu | $0.61^2;0.54^7;0.43^8$ | $+7.1°$ (c = 0.2) |
| 9. | H.Tyr.D-Met.Gly.Phe(4Cl).Pro.NH$_2$ | $0.49^2;0.92^3;0.82^4$ | $+10.0$ (c = 0.2) |
| 10. | Tyr.D-Met(O).Gly.Phe(4Cl).Pro.NH$_2$ | $0.60^4$ | $+11.6°$ (c = 0.1) |
| 11. | Tyr.D-Met(O).Gly.Phe.D-Leu | $0.40^2;0.40^7;0.15^8$ | $+34.2°$ (c = 0.2) |
| 12. | Tyr.D-Met.Gly.Phe(4NO$_2$).Pec.NH$_2$.HCl | $0.52^2;0.93^3$ | $+7.3°$ (c = 0.2) |
| 13. | Tyr.D-Met.Gly.Phe(4NO$_2$).D-Met.NH$_2$.HOOCCH$_3$ | $0.53^2;0.56^7$ | $+35.4°$ (c = 0.2) |
| 14. | Tyr.D-Met.Gly.Phe(4NO$_2$).D-Pro.NH$_2$.HCl | $0.49^2;0.55^7;0.54^8$ | $+45.3°$ (c = 0.2) |
| 15. | Tyr.D-Met(O).Gly.Phe(4NO$_2$).D-Pro.NH$_2$.HOOCCH$_3$ | $0.52^7$ | $+17.3°$ (c = 0.2) |
| 16. | Tyr.D-Met(O).Gly.Phe(4CF$_3$).Pro.NH$_2$.HCl | $0.39^2;0.50^7;0.63^8$ | $+6.43°$ (c = 0.4) |
| 17. | Try.D-Met.Gly.Phe(4SO$_2$Me).Pro.NH$_2$.HOOCCH$_3$ | $0.30^2;0.57^7;0.24^8$ | — |
| 18. | Tyr.D-Met.Gly.Phe(4SOMe).Pro.NH$_2$.HOOCCH$_3$ | $0.27^2;0.58^7;0.34^8$ | — |
| 19. | Tyr.D-Met.Gly.Phe(4SMe).Pro.NH$_2$.HOOCCH$_3$ | $0.27^2;0.55^7;0.75^8$ | $+17.8°$ (c = 1.0) |
| 20. | Tyr.D-Met.Gly.Phe(4CF$_3$).Pro.NH$_2$ HCl | $0.48^2;0.45^7;0.42^8$ | $+4.1°$ (c = 0.4) |
| 21. | Tyr.D-Met.Gly.Phe(4NO$_2$).homoPro.NH$_2$ | $0.52^2;0.15^5$ | $+12.9°$ (c = 0.2) |

EXAMPLE 22

Pharmacological Activity

Peptides of the foregoing Examples were tested for the following activities according to standard pharmacological procedures.

(A) Analgesia in mice in the hot plate test (modification of the method of Eddy, N. B. et al., *J. Pharm. Exp. Therap.* (1953) 107, 385, the peptide being administered by intracerebroventricular injection).

(B) Antidiarrhoeal activity in the rat. In this procedure rats were starved for 24 hours, the peptide then administered either sucutaneously or orally followed after 15 minutes by 1 ml. castor oil per rat given orally.

(C) For anti-tussive testing, guinea-pigs were subjected to an aerosol containing 20% citric acid, 30 minutes after administration of compound (orally or subcutaneously). The number of coughs during a five minute exposure are counted and meaned for six animals per treatment. The method is that described by Boura, A. L. A., Green, A. F. and Saunders, I. A. Br. J. Pharmac., May 1970, Vol. 39, No. 1, page 225.

(D) Analgesia in mice in the writhing test (modification of the method of Henderson et al. (J. Pharm. Exp. Therap., 125, (1959), 237) the peptide being administered orally.

From the data obtained the respective ED$_{50}$ figures were calculated (i.e. the dose required to elicit the appropriate effect in 50% of the animals). N.T.: not tested.

| | RESULTS EXPRESSED AS ED$_{50}$: | | | | |
|---|---|---|---|---|---|
| | ANALGESIA:- MOUSE HOT PLATE | ANTIDIARRHOEA | | ANTITUSSIVE | ANALGESIA:- WRITHING |
| Peptide of Example No. | µg/mouse i.c.v. | mg/kg s.c. | (rat) p.o. | mg/kg (guinea-pig) | mg/kg (mouse) |
| 1 | 0.007 | 0.05 | 2 | 0.7 p.o. | 35 p.o. |
| 2 | 0.005 | 0.02 | 0.05 | 0.7 p.o. 0.02 s.c. | 2 p.o. |
| 3 | 0.005 | 2 | 7 | None at 10 p.o. | NT |
| 4 | 0.07 | 0.2 | None at 10 | NT | NT |
| 5 | 0.05 | 0.03 | 0.3 | >10 p.o. | NT |
| 6 | 0.0007 | 0.05 | 0.2 | 9 p.o. | NT |
| 7 | 0.00008 | 0.05 | 0.3 | 3 p.o. | NT |

-continued

| | RESULTS EXPRESSED AS $ED_{50}$: | | | | |
|---|---|---|---|---|---|
| Peptide of Example No. | ANALGESIA:- MOUSE HOT PLATE µg/mouse i.c.v. | ANTIDIARRHOEA | | ANTITUSSIVE mg/kg (guinea-pig) | ANALGESIA:- WRITHING mg/kg (mouse) |
| | | mg/kg s.c. | (rat) p.o. | | |
| 8 | 0.07 | 5 | >10 | NT | NT |
| 9 | 0.005 | 0.2 | 10 | NT | NT |
| 10 | 0.0008 | 0.02 | 1 | >10 p.o. | NT |
| 11 | 0.001 | 0.7 | >10 | NT | NT |
| 12 | 0.008 | 0.3 | 8 | NT | NT |
| 13 | 0.005 | 1 | >10 | >10 p.o. | NT |
| 14 | 0.003 | 0.02 | 0.2 | <10 p.o. | NT |
| 15 | 0.003 | 0.02 | 0.1 | 10 p.o. | 3 p.o. |
| 16 | 0.003 | 0.03 | 2 | None at 3 p.o. | NT |
| 17 | 0.08 | None at 1 | None at 10 | NT | NT |
| 18 | 0.03 | None at 1 | None at 10 | NT | NT |
| 19 | 0.8 | 8 | None at 10 | NT | NT |
| 20 | 0.07 | 0.1 | 8 | NT | NT |
| 21 | 0.003 | 0.03 | 2 | NT | NT |

EXAMPLE 23

Pharmaceutical Formulations (A) Tablet Formulation (20 mg/tablet)

Compound of formula (I): 20 mg
Lactose: 76 mg
Maize Starch: 10 mg
Gelatin: 2 mg
Magnesium Stearate: 2 mg Mix together the compound of formula (I), Lactose and Maize Starch. Granulate with a solution of the Gelatin dissolved in water. Dry the granules, add the Magnesium Stearate and compress to produce tablets, 110 mg per tablet.

(B) Suppository (5 mg/product)

Compound of formula (I): 250 mg
Suppository Base (Massa Esterinum C): to 100 g

Melt the suppository base at 40° C. Gradually incorporate the compound of formula (I) in fine powder form and mix until homogeneous. Pour into suitable moulds, 2 g per mould, and allow to set.

Massa Esterinum C is a commercially available suppository base consisting of a mixture of mono, di, and triglycerides of saturated vegetable fatty acids. It is marketed by Henkel International, Dusseldorf.

(C) Pessary (5 mg/product)

Compound of formula (I): 5 mg
Lactose: 400 mg
Povidone: 5 mg
Magnesium Stearate: 5 mg Mix together the compound of formula (I) and Lactose. Granulate with a solution of Povidone in 50% aqueous ethanol. Dry the granules add the magnesium Stearate and compress on suitably shaped punches, 415 mg per pessary.

(D) Freeze-dried Injection 100 mg/vial

Compound of formula (I): 100 mg
Water for Injections to: 2.0 ml

Dissolve the compound of formula (I) in the Water for Injections. Sterilise the solution by passage through a membrane filter, 0.2 µm pore size, collecting the filtrate in a sterile receiver. fill into sterile glass vials, 2 ml/vial under aseptic conditions and freeze-dry. Close the vials with sterile rubber closures secured with an aluminium seal.

The injection is reconstituted prior to administration by the addition of a convenient volume of Water for Injections or sterile saline solution.

In the foregoing, the weight of the compound of formula (I) is in each instance calculated with reference to the peptide base.

What we claim is:

1. Tyr.D-Met. Gly. Phe(4NO$_2$). ProNH$_2$.

2. A pharmaceutically acceptable acid addition said of Tyr.D-Met. Gly.Phe(4NO$_2$). ProNH$_2$.

3. The acetate salt of claim 2.

4. A pharmaceutical composition for use as an antidiarrhoeal comprising an effective antidiarrhoeal amount of H.Tyr.D-Met.Gly.Phe(4NO$_2$).Pro.NH$_2$ or a pharmaceutically acceptable acid addition salt thereof together with a pharmaceutically acceptable liquid or solid carrier therefor.

5. The composition of claim 4 in a form suitable for oral, rectal or parenteral administration.

6. The composition of claim 5 in the form of a tablet.

7. The composition of claim 5 in the form of a capsule.

* * * * *